United States Patent [19]
Rothstein et al.

[11] Patent Number: 5,888,721
[45] Date of Patent: Mar. 30, 1999

[54] ANTIBACTERIAL COMPOUNDS

[75] Inventors: David Rothstein, Lexington; Nagraj Mani, Somerville; Zhi-Dong Jiang, Watertown, all of Mass.

[73] Assignee: Millennium Pharmaceuticals, Inc., Cambridge, Mass.

[21] Appl. No.: 674,831

[22] Filed: Jul. 3, 1996

[51] Int. Cl.$^6$ ............................ C12Q 1/04; C12Q 1/02; A61K 31/425; C07C 229/00
[52] U.S. Cl. ................................... 435/4; 435/29; 435/32; 514/372; 560/39; 560/42
[58] Field of Search ................................. 435/4, 32, 29; 514/372; 560/39, 42

[56] References Cited

U.S. PATENT DOCUMENTS

| | | | |
|---|---|---|---|
| 5,473,096 | 12/1995 | Matsutani et al. | 560/39 |
| 5,534,533 | 7/1996 | Ohtani et al. | 514/372 |
| 5,597,943 | 1/1997 | Ohtani et al. | 560/42 |

OTHER PUBLICATIONS

Matsumoto et al. "Isolation & Biological Activity of Theieloci . . . " J. Antibiotics 48(2) 106–112, Feb. 1995.

*Primary Examiner*—Nancy Degen
*Attorney, Agent, or Firm*—Fish & Richardson P.C.

[57] ABSTRACT

The invention features two novel antibiotics, termed 15352A and 15352B, having the structures shown in the figures.

7 Claims, 7 Drawing Sheets

|   | 1 | 2 | 3 | 4 | 5 | 6 | 7 | 8 | 9 | 10 | 11 | 12 |
|---|---|---|---|---|---|---|---|---|---|---|---|---|
| A | 0.352 | 0.347 | 0.319 | 0.316 | 0.331 | 0.067 | 0.066 | 0.121 | 0.163 | 0.132 | 0.183 | 0.270 |
| B | 0.315 | 0.318 | 0.319 | 0.281 | 0.263 | 0.064 | 0.068 | 0.100 | 0.140 | 0.158 | 0.129 | 0.259 |
| C | 0.311 | 0.328 | 0.302 | 0.303 | 0.250 | 0.062 | 0.068 | 0.107 | 0.163 | 0.150 | 0.104 | 0.266 |
| D | 0.320 | 0.318 | 0.324 | 0.307 | 0.149 | 0.051 | 0.072 | 0.137 | 0.199 | 0.116 | 0.067 | 0.161 |
| E | 0.310 | 0.306 | 0.307 | 0.298 | 0.146 | 0.062 | 0.089 | 0.092 | 0.103 | 0.118 | 0.111 | 0.253 |
| F | 0.311 | 0.295 | 0.281 | 0.274 | 0.176 | 0.060 | 0.068 | 0.092 | 0.142 | 0.128 | 0.142 | 0.196 |
| G | 0.307 | 0.303 | 0.298 | 0.289 | 0.148 | 0.065 | 0.070 | 0.076 | 0.064 | 0.105 | 0.135 | 0.177 |
| H | 0.338 | 0.291 | 0.287 | 0.294 | 0.108 | 0.076 | 0.072 | 0.075 | 0.068 | 0.105 | 0.137 | 0.160 |

FIG. 1A

|   | 1 | 2 | 3 | 4 | 5 | 6 | 7 | 8 | 9 | 10 | 11 | 12 |
|---|---|---|---|---|---|---|---|---|---|---|---|---|
| A | 0.340 | 0.323 | 0.310 | 0.328 | 0.325 | 0.319 | 0.325 | 0.299 | 0.292 | 0.269 | 0.152 | 0.196 |
| B | 0.333 | 0.304 | 0.304 | 0.307 | 0.310 | 0.301 | 0.322 | 0.317 | 0.287 | 0.395 | 0.077 | 0.184 |
| C | 0.316 | 0.306 | 0.306 | 0.306 | 0.306 | 0.301 | 0.314 | 0.292 | 0.206 | 0.434 | 0.067 | 0.157 |
| D | 0.315 | 0.313 | 0.309 | 0.311 | 0.307 | 0.299 | 0.318 | 0.296 | 0.175 | 0.751 | 0.074 | 0.146 |
| E | 0.321 | 0.309 | 0.311 | 0.305 | 0.299 | 0.295 | 0.313 | 0.296 | 0.182 | 0.415 | 0.069 | 0.151 |
| F | 0.314 | 0.306 | 0.305 | 0.304 | 0.297 | 0.297 | 0.303 | 0.296 | 0.190 | 0.104 | 0.110 | 0.154 |
| G | 0.312 | 0.307 | 0.305 | 0.303 | 0.301 | 0.301 | 0.311 | 0.294 | 0.157 | 0.083 | 0.150 | 0.144 |
| H | 0.341 | 0.314 | 0.316 | 0.332 | 0.312 | 0.306 | 0.333 | 0.322 | 0.126 | 0.081 | 0.117 | 0.115 |

FIG. 1B

Summary page for bioprofiling of AA14649

| Requested by: | Zhi-Dong | | | Date in: | 8/28/95 | | Date out: | 9/5/95 | |
|---|---|---|---|---|---|---|---|---|---|
| Plate ID | 14649-2 | | | | | | | | |
| | 14649-2 | | 14649-2 | 14649-2 | 14649-2 | | | 14649-2 | 14649-2 |
| Fraction | CALB | Afum | Entv | Staph | Ecoli | CACS | ATUB | Cytotox | Cidality* |
| 6-163-7a | 1.1 | | 2.7 | 2.7 | 3.4 | | | 0.0 | |
| control | | | | | | | | | |

FIG. 2A

Summary page for bioprofiling of AA15352

| Requested by: | Zhi-DOng | | | Date in: | 8/28/95 | | Date out: | 9/5/95 | |
|---|---|---|---|---|---|---|---|---|---|
| Plate ID | 15352-2 | | | | | | | | |
| | 15352-2 | | 15352-2 | 15352-2 | 15352-2 | | | 15352-2 | 15352-2 |
| Fraction | CALB | Afum | Entv | Staph | Ecoli | CACS | ATUB | Cytotox | Cidality* |
| 76-163-1-10 | 2.1(weak) | | 2.0 | 1.8 | 0.2 | | | 1.1 | |
| 76-163-1-11 | 0.8 | | 2.7 | 2.1 | 0.3 | | | 1.7 | |
| control | | | | | | | | | |

Summary page for bioprofiling of AA 15352

| Requested by: | ZDJ | | Date in: | 13-Nov | | Date out: 20/11/95 | | | |
|---|---|---|---|---|---|---|---|---|---|
| Plate ID | 15352-3 | | | | | | | | |
| | 15352-3 | | 15352-3 | 15352-3 | 15352-3 | | | 15352-3 | 5352-3 |
| Fraction | CALB | Afum | Entv | Staph | Ecoli | CACS | ATUB | Cytotox | Cidality* |
| 15352A | 2.0 | | 2.5 | 2.4 | 0.2 | | | 1.3 | |
| 15352B | 1.3 | | 3.2 | 3.2 | 0.1 | | | 2.2 | |
| thielavin A | 0.4 | | 3.8 | 2.5 | 0.0 | | | 2.4 | |
| thielavin B | 0.5 | | 3.4 | 2.0 | -0.1 | | | 1.3 | |
| thielavin C | 0.0 | | 3.1 | 2.3 | -0.1 | | | 1.7 | |

CA - first two letters of the organism tested

8/3: the first number indicates dilution well;
the second number indicates loss in logs of CFU (3 is considered cidal)

|  | | MIC (ug) | | | |
|---|---|---|---|---|---|
| 15352A | 52.9 | 6.4 | 9.0 | 812.3 | 135.4 |
| 15352B | 204.0 | 1.5 | 1.6 | 1102.6 | 20.3 |
| thielavin A | 1420.8 | 0.5 | 6.5 | 1480.6 | 12.1 |
| thielavin B | 1190.1 | 1.1 | 21.1 | 1590.9 | 133.9 |
| thielavin C | 3270.4 | 1.8 | 10.2 | 1568.2 | 54.2 |

ANTIBACTERIAL COMPOUNDS

BACKGROUND OF THE INVENTION

This invention relates to antibacterial compounds.

Microorganisms, such as fungi, produce diverse secondary metabolites that are capable of modulating many different biological activities. For example, it is known that secondary metabolites isolated from the fermentation broth of *Thielavia terricola* inhibit phospholipase $A_2$ and prostaglandin biosynthesis, and thus may be useful in the treatment of inflammation. The largest group of bioactive secondary metabolites are antibiotics that inhibit the growth of bacteria, fungi, and viruses by acting on essential processes such as cell wall synthesis, DNA replication, and protein synthesis.

The search for new and useful metabolites has been fueled by the need for more potent (and less toxic) antibiotics, the evolution of microorganisms that are resistant to existing antibiotics, and the emergence of new viral diseases. Corresponding factors from the agricultural sector have also contributed to the urgent search for new bioactive secondary metabolites (Franco et al., 1991, Crit. Rev. in Biotech. 11(3):193–276). Investigators who search for these compounds are likely to be rewarded: only about 5% of the estimated 1.5 million species of fungi have been described (Hawksworth, 1991, Mycol. Res. 95:441–452) and less than 10% of these have been tested for the production of useful secondary metabolites (Porter, 1993, Pestic. Sci. 39:161–168).

SUMMARY OF THE INVENTION

The invention features two novel antibiotics, termed 15352A and 15352B, having the structures shown in the figures, below.

DETAILED DESCRIPTION

Brief Description of the Drawings

FIG. 7A is a line graph depicting the induction of A256 cells by vancomycin. Filled squares (Van10–Van0) plot the optical density, over time, of an A256 culture that was grown overnight in BHI medium containing 10 µg/ml vancomycin and then shifted to vancomycin-free BHI medium. Open squares (Van10–Van256) plot the optical density, over time, of an A256 culture that was grown overnight in BHI medium containing 10 µg/ml vancomycin and shifted to BHI containing 256 µg/ml vancomycin. Closed circles (0–0) plot the optical density, over time, of an A256 culture that was grown overnight in vancomycin-free BHI medium and then shifted to vancomycin-free BHI medium. Open circles (0–Van256) plot the optical density, over time, of an A256 culture grown overnight in vancomycin-free BHI medium and shifted to BHI medium containing 256 µg/ml vancomycin.

Fermentation and Preparation of Fungal Extracts

Typically, fungi are fermented in illuminated incubators at 30° C. A large number of fungi can be grown simultaneously by placing a single fungal colony into each well of a 96-well microtiter plate. The colonies are grown in 200 µl of medium, and can be transferred to agar slants, which are used to inoculate larger liquid fermentation cultures. For example, 250 ml conical flasks containing 50 ml of medium (corn steep liquor (CSL; Sigma Chemical Co.) and corn meal medium) can be inoculated with 5 ml of a spore suspension derived from an agar slant, and placed on a rotary shaker in an illuminated 30° C. growth chamber for one week. Extracts can be prepared from either the total fermentation, including the broth and fungi (e.g., whole broth butanol extracts (WBBE)), from the fermentation broth alone, or from isolated fungi using solvents, such as ethyl acetate, acetone, or butanol, according to standard methods. Whole broth cultures are homogenized prior to extraction to break up mycelia. The extracts are then subjected to analysis for antibacterial activity.

Assays for Antibacterial Activity

Antibacterial activity can be identified by a number of standard assays that detect either inhibition of bacterial growth or destruction of existing bacteria. Inhibition of growth can be demonstrated by comparing the optical density of liquid bacterial cultures growing in the presence of a potential antibacterial compound with those growing in its absence. The lower the relative optical density, the more effective the antibiotic. An antibacterial compound can also be detected by contacting a lawn of bacteria with either whole broth, an unextracted homogenate, or a purified compound, and measuring the area of bacterial lysis. Typically, to perform this assay, a 25 ml culture of bacteria (e.g., *Bacillus subtilis* in Luria broth (LB)) is grown overnight, subcultured as a 1% inoculum in fresh medium, and allowed to grow until reaching an optical density at 650 nm of 1.0–1.5. The cells are collected into a pellet by centrifuging the culture (e.g. at 9000×g for 5 minutes at 30° C.). The supernatant is then decanted, leaving about 1 ml of spent broth behind and the cell pellet is resuspended and added to a solution of top agar (LB with 0.7% agar) at 50° C. The suspension is spread over a bacterial culture plate and incubated until a turbid lawn of bacteria is visible. Homogenized extracts (approximately 10 $\mu$l) from fermented fungi are spotted onto the bacterial lawn, and the plate is covered, incubated at 37° C. for several hours, and then checked for areas of lysis, apparent as a clear zone, around the spot of broth, homogenate, or purified compound. Alternatively, the extracts may be spotted on the plate before the lawn forms. The lysis zones are assessed by measuring their diameter; the larger the area, the more effective the antibiotic.

In addition to detecting general effects on bacterial growth or viability, it is possible to perform assays that detect an effect on specific bacterial structures, enzymes, or processes. A variety of approaches have been used by skilled artisans to obtain antibiotics that act on the bacterial cell wall, on protein biosynthesis, on selective bacterial groups such as pseudomonads and anaerobes, or on bacterial nucleic acid synthesis (Franco et al., 1991, Crit. Rev. in Biotech. 11(3):193–276). In addition, assays are available to detect compounds that have robust activity in vivo, and thus that would be effective therapeutics.

Identification of Compounds Responsible for a Given Biological Activity

Once a biological activity is detected in a fungal culture, the compound responsible for that activity is isolated, purified, and assigned a molecular identity. This process begins with the recovery of the secondary metabolite from the fermentation mass by solvent-based extraction or by adsorption on ion exchange resins or charcoal. The objective of the isolation procedure is to obtain a manageable amount of the compound in a form suitable for purification by chromatographic procedures. These procedures are well known to skilled artisans and include liquid—liquid, liquid-solid, or affinity chromatography. Normal phase, reversed-phase, ion-exchange, and gel filtration techniques may also be implemented as needed (Box, 1985, Approaches to the Isolation of an Unidentified Microbial Product, in *Discovery and Isolation of Microbial Products*, M. S. Verall, Ed., Ellis Horwood, Chichester; Franco et al., 1991, Crit. Rev. in Biotech. 11(3):193–276). The purification process is typically monitored by examining the activity of chromatographically fractionated components in a biological assay, such as those described above, or in the Examples below.

The identification of the metabolite in question involves comparison with previously reported metabolites and the assignment of a molecular structure. This can be accomplished using standard methods, including nuclear magnetic resonance (NMR) spectoscopy, mass spectrometry (MS), and X-ray crystallography (A. Aszalos, Ed., 1986, Modern Analysis of Antibiotics, Marcel Dekker, New York; Franco et al., supra). The concept of comparison without effecting a complete separation originated with thin layer chromatography (TLC) and was replaced by HPLC, combined ideally with a mass spectrometer. HPLC is currently applied widely in the study of secondary metabolites, including antibiotics, in part because the use of retention time alone can be used to infer the identity of almost all the major classes of antibiotics. To unambiguously identify a chemical structure, spectroscopic techniques (including proton ($[^1H]$)-NMR carbon 13 ($[^{13}C]$)-NMR, infrared (IR), and high resolution mass spectrometry (HRMS)) or X-ray crystallography are required.

EXAMPLE 1

Novel Antibacterial Compounds from Cultures of *Thielavia terracola*

Initially, antibacterial activities were discovered in cultures of *Thielavia terracola* by a high throughput screening program. Subsequently, one liter fermentation cultures were prepared for HPLC analysis, which, in combination with an antibacterial panel screen, resulted in the preliminary identification of active antibacterial compounds. A 10 liter fermentation culture was then prepared in order to obtain sufficient material for unequivocal identification of five compounds by NMR and MS analysis.

Preliminary Identification of Five Active Compounds by HPLC Analysis

Extracts from the supernatant of one liter fermentation cultures of *T. terracola* (designated AA14649 and AA15352) were prepared for HPLC analysis by taking whole broth butanol extracts to dryness and then resuspending them, by sonication, in HPLC-grade methanol. These samples were analyzed with a Dynama™ C-18 reversed-phase column using a stepped gradient that began with sample loading and washing with 95% water/5% methanol followed after 8 minutes with a linear gradient to 100% methanol. The rate of flow was 8 ml/minute and 0.5 minute fractions were collected. A 100 $\mu$l aliquot of each fraction, beginning with the seventeenth fraction, was transferred into each well of a 96-well microtiter plate in preparation for an antibacterial screening assay.

ENTV Screening: An Antibacterial Panel Screen

Fungal extracts, prepared as described above, were tested for their ability to inhibit the growth of *Enterococcus faecium*, *Eschericia coli*, and *Staphylococcus aureus*. The strain of *E. faecium* used is identical to H80721 by molecular typing techniques, but does not appear to be gentamicin resistant (Green et al., 37:1238–1242). *E. coli* is also available from the American Type Culture Collection in Manassas, Va. (ATCC Number 533499). *S. aureus* utilized were of the FDA strain PCI 1158 (ATCC Number 14775). *Thilavia terricola* strain AA 15352 is available from the ATCC (ATCC Number 74427).

The bacteria were stored as cryoprotected frozen stocks. The stocks, prepared from a single isolated colony, were used to prepare liquid bacterial cultures, as follows. Bacteria from a frozen stock was spread onto the surface of a brain heart infusion (BHI) agar plate with a sterile loop so that isolated colonies developed following incubation at 37° C. overnight. Bacteria from isolated colonies were amplified further by incubation in 1 ml of liquid medium overnight at 37° C., with agitation. Unless otherwise noted, cultures of *S. aureus* were grown in LB and cultures of *E. faceium* and *E. coli* were grown in BHI medium at 37° C. with agitation. The following day, log phase cultures were prepared by diluting the 1 ml culture into fresh pre-warmed media. *E. faecium* was diluted 1:10, *E. coli* was diluted 1:100, and *S. aureus* was diluted 1:250. Following a 2–3 hour incubation period, the OD at 650 nm was measured, and working suspensions were made by diluting the cultures to a final OD reading of 10 mOD for *E. faecium* and *S. aureus* and 0.5 mOD for *E. coli*. (1 mOD=0.001 OD unit). All optical density measurements were obtained with the ThermoMa™ Microtiter Plate Reader from Molecular Devices.

Approximately 150 μl of working suspension was aliquoted into each well of a microtiter plate containing the HPLC fractions described above, which was incubated for approximately 6 hours, without agitation. Prior to incubation, the OD measurements ranged from 0.045–0.041; following incubation these measurements ranged from 0.30 to 0.38. One row of each microtiter plate may serve as an "untreated" control, lacking fungal extract. The average OD obtained from "untreated" cultures can be used to calculate the relative death of the bacteria in wells containing (or lacking) fungal extract. A known antibacterial compound, such as ciprofloxacin, may be used as a positive control.

Antibacterial activity was assessed by subtracting the initial O.D. reading in each well from the final O.D. reading in that well. If the initial and final readings were similar (giving a difference near zero), then the extract must have contained a compound that inhibited growth. Conversely, if the final value was much larger than the initial value, the extract had little or no effect on bacterial growth.

Figure 1A:
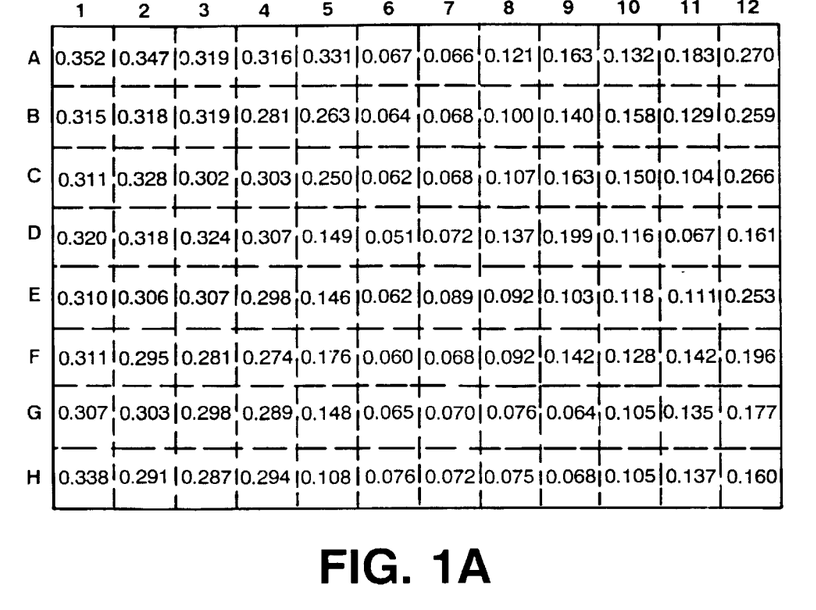
FIG. 1A is a grid representing a 96-well microtiter plate. The number in each square of the grid is the difference between the final optical density of a bacterial culture grown in the presence of HPLC fractions collected from a culture of *T. terracola* (designated AA14649) and the initial optical density of that culture.
Figure 1B:
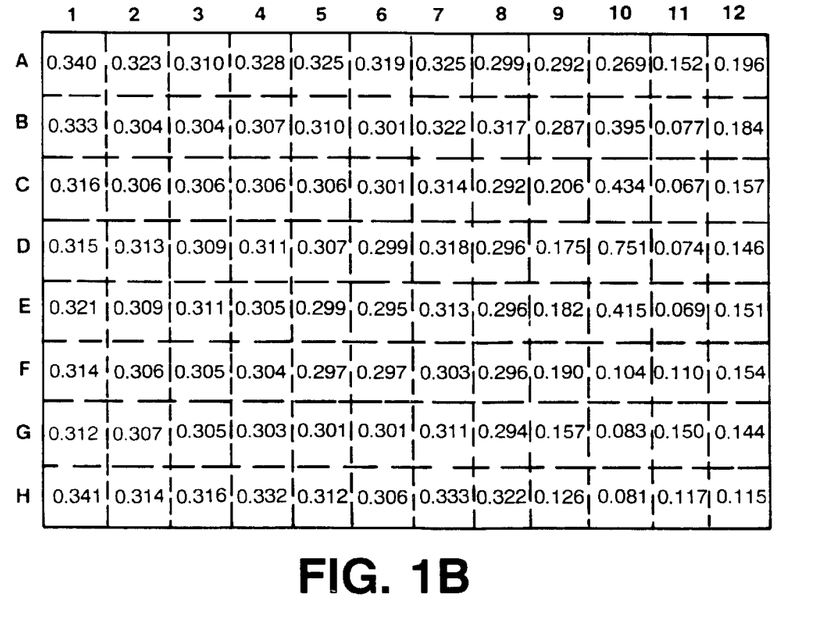
FIG. 1B is a grid representing a 96-well microtiter plate. The number in each square of the grid is the difference between the final optical density of a bacterial culture grown in the presence of HPLC fractions collected from a culture of *T. terracola* (designated AA15352) and the initial optical density of that culture.
Figure 2A:
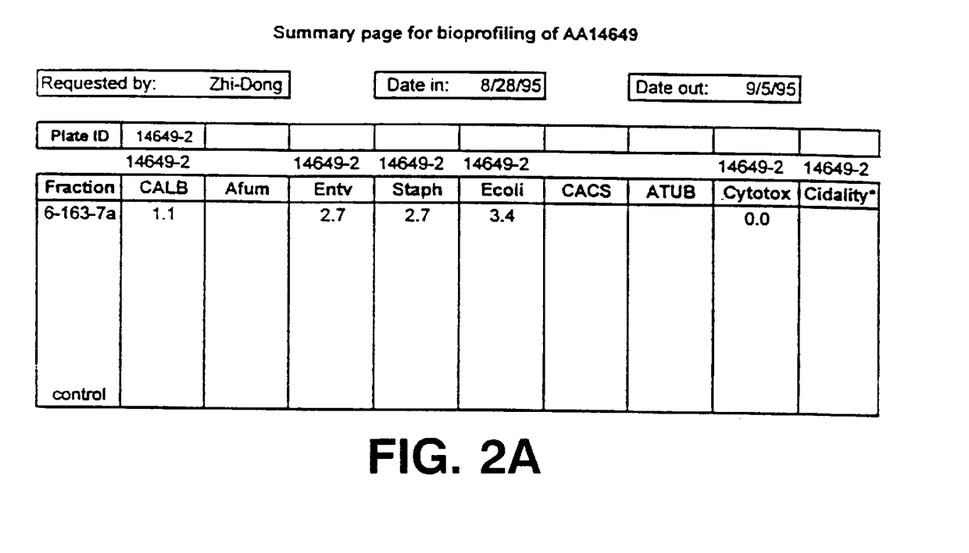
FIG. 2A is a summary of the bioprofile obtained from an active fraction (6-163-7a) isolated by HPLC from a culture of *T. terracola* (designated AA14649).
Figure 2B:
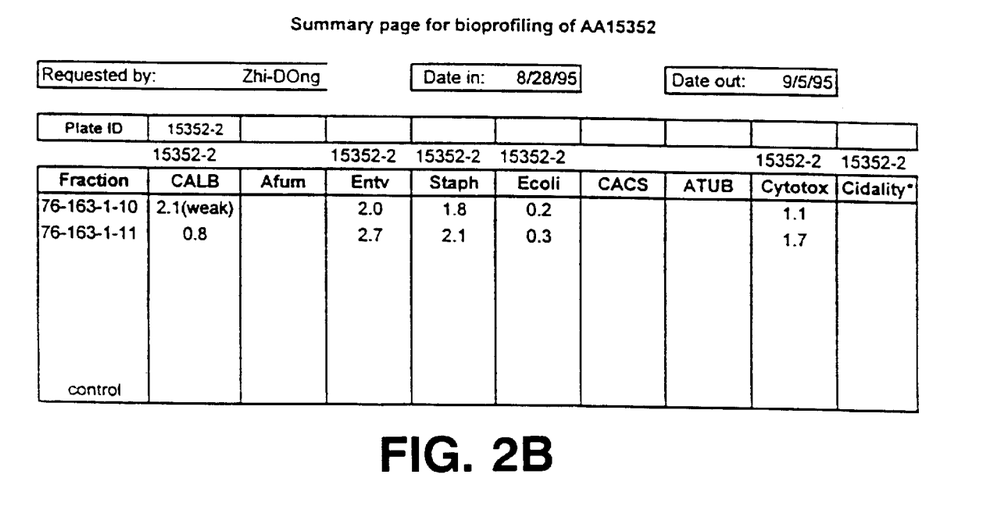
FIG. 2B is a summary of the bioprofile obtained from two active fractions (76-163-1-10 and 76-163-1-11) isolated by HPLC from a culture of *T. terracola* (designated AA15352).

The calculated (final minus initial) optical density readings for HPLC fractions that were collected from AA14649 and AA15352 and added to microtiter plates containing bacteria are shown in FIG. 1A (AA14649) and FIG. 1B (AA15352). A summary of the bioprofiles obtained from active fractions from these cultures is shown in FIG. 2A (AA14649) and FIG. 2B (AA15352).

Unequivocal Identification of Five Antibacterial Compounds by Nuclear Magnetic Resonance Spectroscopy and Mass Spectrometry According to the NMR pattern and mass spectral data, the two active compounds present in fractions 76-163-1-10 and 76-163-1-11 are closely related to thielavin B. A 10 liter fermentation culture of AA15352 was prepared in order to obtain a greater quantity of material for analysis. Approximately 6 liters of supernatant were obtained from this culture and partitioned against an equal volume of ethyl acetate (pH 6.0). The ethyl acetate was then evaporated to yield 100 mg of extract residue. The aqueous layer was adjusted to pH 4.0, extracted again with ethyl acetate, and concentrated by evaporation to yield 10–20 mg of material.

Methanol (2 liters×2) was used to extract mycelium. The solution was then filtered and the methanol was removed by evaporation. The resulting aqueous layer was extracted twice with equal volumes of ethyl acetate, which was removed to give 1.9 grams of extract.

Figure 3:
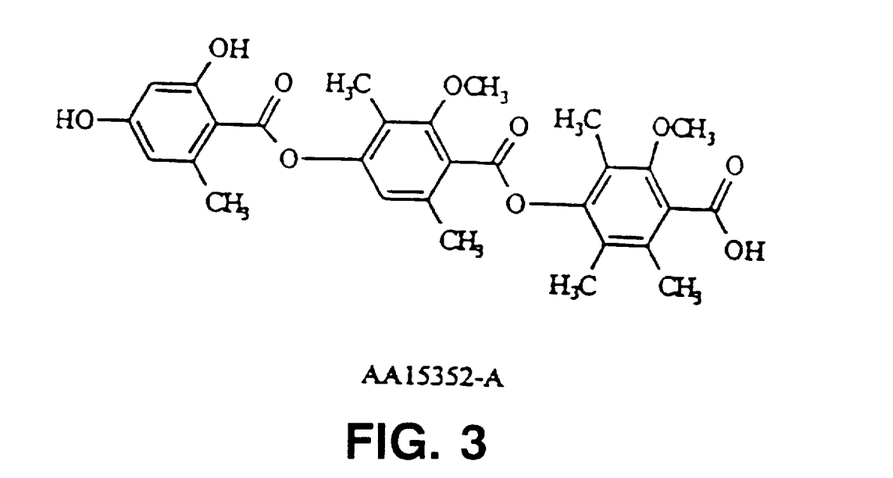
FIG. 3 is a representation of the structure of a novel compound, designated 15352A.

Mass spectral data was acquired for fractions 74 to 86. The spectra showed that fractions 78 and 79 contained most of the material which gave a negative ion M/Z 537. A $^1$H-NMR spectrum showed that the material contained within these fractions was impure. However, a compound containing 6 methyl groups was predominant. There were clearly three aromatic protons, two of which were meta-coupled and one that was isolated. The MS negative ions at M/Z [?] 537 (MW 538), 387, and 195 clearly suggested the structure shown in FIG. 3, which is a novel compound designated 15352A.

Figure 4:
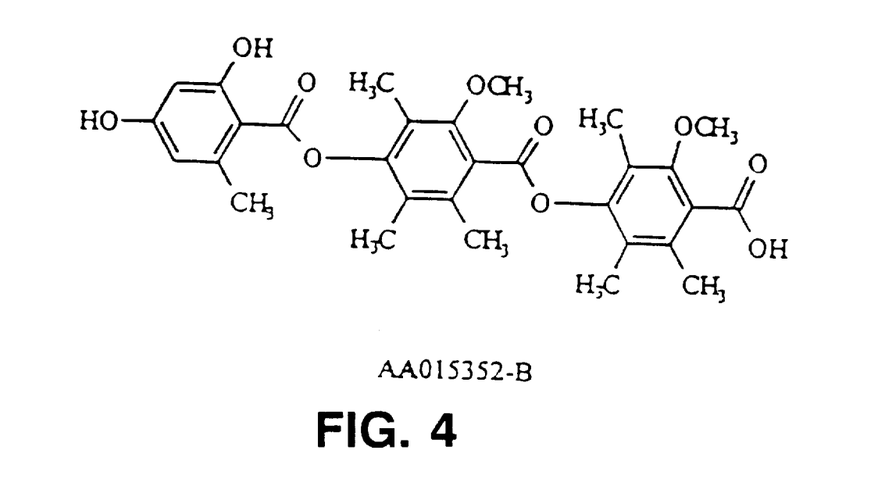
FIG. 4 is a representation of the structure of a novel compound, designated 15352B.

Mass spectroscopy, $^1$H-NMR and $^{13}$C-NMR data were also acquired for fraction 82. M/Z 551 in the negative ion mode clearly showed MW 552. Examination of both $^1$H- and $^{13}$C-NMR spectra revealed 7 methyl groups, 2 methoxy groups, and 2 meta-coupled aromatic protons. The number of $^{13}$C count was approximately 30 (two of which overlapped). According to these data, the compound in fraction 82 is similar to thielavin B but differs in the number and substitution pattern of methyl groups. The structure of this novel compound, designated 15352B, is shown in FIG. 4.

The weight of 21-9E was measured. There was approximately 14 mg of material, which suggested that the MIC for this fraction's material was about 1 μg/ml. $^1$H-NMR analysis of the material in the neighbor fraction, 9D, showed that the material is fairly pure and identical to thielavin B.

Other fractions of 103-21 were also analyzed by $^1$H-NMR. Spectra of 103-21-10B and 103-21-11D revealed that these two fractions each contained thielavin C and di-de-O-methyl thielavin C.

Figure 5:
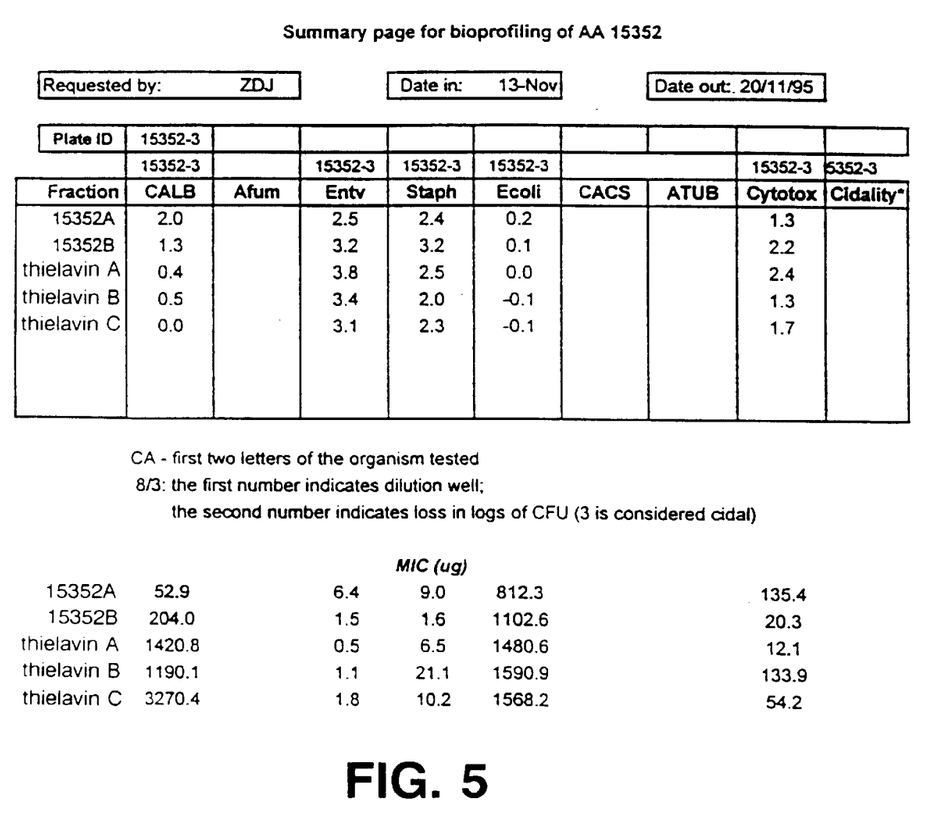
FIG. 5 is a summary bioprofile obtained for the five active compounds (15352A, 15352B, thielavin A, thielavin B, and thielavin C) isolated from cultures of *T. terracola*.

Bioprofiles of the five compounds isolated from AA15352 (15352A, 15352B, thielavin A, thielavin B, and thielavin C; FIG. 5), demonstrated that free phenolic hydroxy groups elevated the potency against ENTV and cytotoxicity. However, generally, the structural variations among the compounds did not cause dramatic variation in their bioactivity.

EXAMPLE 2

An Assay for Antibacterial Cell Wall Activity

Extracts from cultures of *T. terricola* were active in an assay designed to detect compounds that inhibit synthesis of the bacterial cell wall. These extracts (from cultures designated AA15222, AA15352, AA16598, and AA16615) contained one or more compounds having HPLC and mass spectral data consistent with thielavin B or a related compound. In addition, thielavin B was shown to act synergistically with vancomycin (a compound that inhibits bacterial cell wall biosynthesis by inhibiting the transglycosylation reaction) to inhibit multiply drug-resistant *E. faecium*.

In the assay described herein, bacterial cell growth is dependent on sub-MIC concentrations of a cell wall-active compound such as vancomycin, described above, or moenomycin. The assay is based on the hypothesis that vancomycin-dependent bacteria would grow in the presence of novel bacterial cell wall inhibitors even if these inhibitors were not chemically related to vancomycin.

The bacterial strain utilized in this screen is A256-5, a strain of *E. faecium* A256 that was selected by super-resistance to vancomycin. A256-5 cells were isolated at ChemGenics and received from Dr. David Shlaes. Vancomycin resistance can also be induced by teicoplainin.

To prepare for the assay, A256-5 cells were grown in the presence of vancomycin, washed extensively, resuspended at a very low concentration (so that the optical density is approximately 0.00001), and aliquoted into the wells of a microtiter plate. Growth was not detected, even after a 17 hour incubation, unless vancomycin (>1 μg/ml) or moenomycin (0.01–1.0 μg/ml) was present. Fungal extracts are then assayed for the presence of antibacterial compounds by application to the A256-5 cells.

Frozen stocks of A256-5 (cryoprotected with 20% glycerol) were made according to standard mentods from liquid cultures initiated with a single isolated bacterial colony. A sterile loop was used to transfer bacteria from the frozen stock to a 10 ml culture of BHI containing vancomycin (64 μg/ml), which was incubated at 37° C., with shaking, for approximately 2.5 hours. When the bacterial culture was in the log phase of growth, the cells were harvested by centrifugation (e.g., at 3700 rpm for 10 minutes in a Beckman GS6R centrifuge) and resuspended in 10 ml of vancomycin-free BHI medium. The cells were pelleted and resuspended twice more, for a total of three washes in vancomycin-free BHI medium. The OD was measured at 650 nm and, based on this reading, the dilution required to bring the OD to 0.00001 (0.01 mO.D.) was calculated. Once diluted, the cells were aliquoted into the wells of a microtiter plate (75 μl cell suspension/well) and the samples to be tested were added, preferably in duplicate. The following controls were also included: moenomycin at a final concentration of 0.27, 0.09, 0.03, or 0.01 μg/ml/well and wells containing vancomycin at a final concentration of 1 or 10 μg/ml. The OD at 650 nm is read using the Biorad Model 3550-UV plate reader before and after incubation at 37° C. for 18–20 hours.

Figure 6:
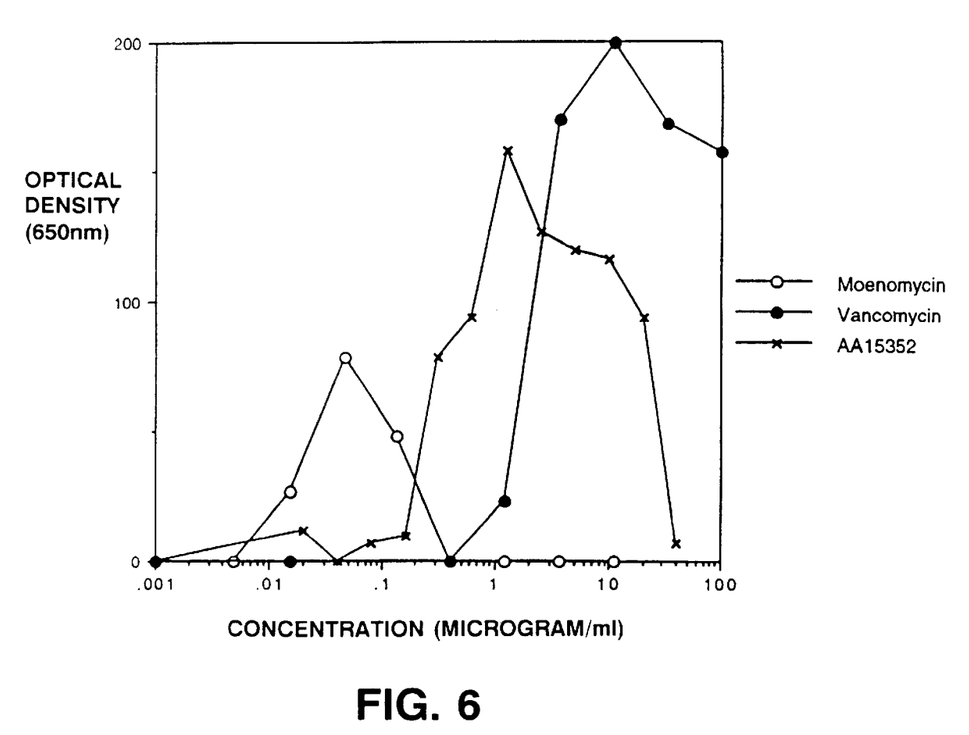
FIG. 6 is a line graph depicting the growth of vancomycin-dependent bacteria (strain A256-5; as reflected by the optical density (OD) of the culture at 650 nm) in the presence of vancomycin (filled circles) or moenomycin (open circles), or in their absence (-X-).

To determine whether bacterial cell growth was stimulated, the initial OD reading was subtracted from the final OD reading. Samples considered "positive" were those that stimulated the bacterial culture to attain an OD of at least 0.04, for both of the duplicate samples. Cells cultured with 0.09 and 0.03 μg/ml moenomycin were stimulated to grow, as expected, as were those containing either 1 or 10 μg/ml vancomycin (FIG. 6). Other drugs tested for their ability to rescue the vancomycin-dependent strain included chloramphenicol, kanamycin, spectinomycin, ampicillin, fosfomycin, erythromycin, fusidic acid, rifampicin, tetracycline, and bacitracin.

Including samples at a 10-fold concentration difference allows observation of growth stimulation by putative cell wall inhibitors at the lower concentration, and growth inhibition at the higher concentration. Alternatively, the higher sample concentration might be required to promote growth of the vancomycin-dependent strain.

Upon refermentation, extracts of the cultures exhibiting activity were subjected to the reversed-phase HPLC system. Antibacterial activity eluted in a region centered at fraction 115. Overlapping this region, in a broader peak, was ENTD activity. This observation suggests that a family of compounds with similar chromatographic properties is responsible for both ENTD and ENTV activities.

Thielavin B and related compounds responsible for ENTV activity were previously purified from AA15352, as described in Example 1. Therefore, ENTD/ENTV active fractions from DEREP of all four cultures (AA15222, AA15352, AA16598, and AA16615) were subjected to mass spectral analysis, which revealed a peak with a molecular weight consistent with thielavin B, or a derivative thereof, in each sample. Purified thielavin B (in HCl salt form; Sigma Chemical Co.) was tested in two-fold dilutions for ENTD and ENTV activities. The MIC for thielavin B in ENTV was 20 μg/ml, while the ENTD activity was detectable at 0.31 μg/ml.

Synergistic activity of thielavin B and vancomycin against the ENTV strain, E. faecium 34044, provided independent evidence that thielavin B interferes with the function or biosynthesis of the cell wall. Given that 15352A and 15352B are structurally similar to thielavin B, it is expected that they will also act synergistically with vancomycin.

EXAMPLE 3

An Assay for Detecting Antibacterial Cell Wall Inhibitors by Activation of a Reporter Gene Upstream from the van Promoter Expression of the vancomycin resistance genes depends on the presence of vancomycin (or moenomycin). Therefore, compounds that induce expression from the van promoter are candidates for inhibitors of bacterial cell wall synthesis.

The discovery that vancomycin resistance genes could be induced in E. faecium strain A256 cells was based on the observation that cells transferred from vancomycin-free medium to vancomycin-containing medium experience a growth lag, while cells "pre-grown" with vancomycin do not experience a lag when transferred to vancomycin-containing medium. In addition, vancomycin-dependent mutants, which are also referred to as super-resistant strains, have been isolated from strain A256, as described above.

Reduction of Lag Phase Growth when E. faecium strain A256 is Challenged with Vancomycin A bacterial plate containing BHI medium and 1.5% agar was streaked with E. faecium strain A256 and incubated overnight at 37° C. Single colonies were picked from the plate and used to inoculate 5 ml liquid cultures of BHI medium containing putative "inducers" of van genes. Cultures containing 10 μg/ml vancomycin, a known inducer of the van genes, served as a positive control. These cultures were incubated at 37° C. for approximately 17 hours. The OD at 650 nm was measured, the culture was diluted to an OD of 0.02, and 100 μl aliquots were transferred to the wells of a microtiter plate. Some of the diluted cultures were challenged with vancomycin, which was added to a final concentration of 256 μg/ml. The plates were incubated at 37° C. and the OD at 650 nm was read approximately once each hour to derive a growth curve. These data were used to construct a semi-log plot of cell growth, where OD was plotted on a logarithmic scale, and time was plotted linearly. If a compound capable of inducing vancomycin resistance was present, then the cells accomodated vancomycin exposure by growing more rapidly.

Figure 7A:
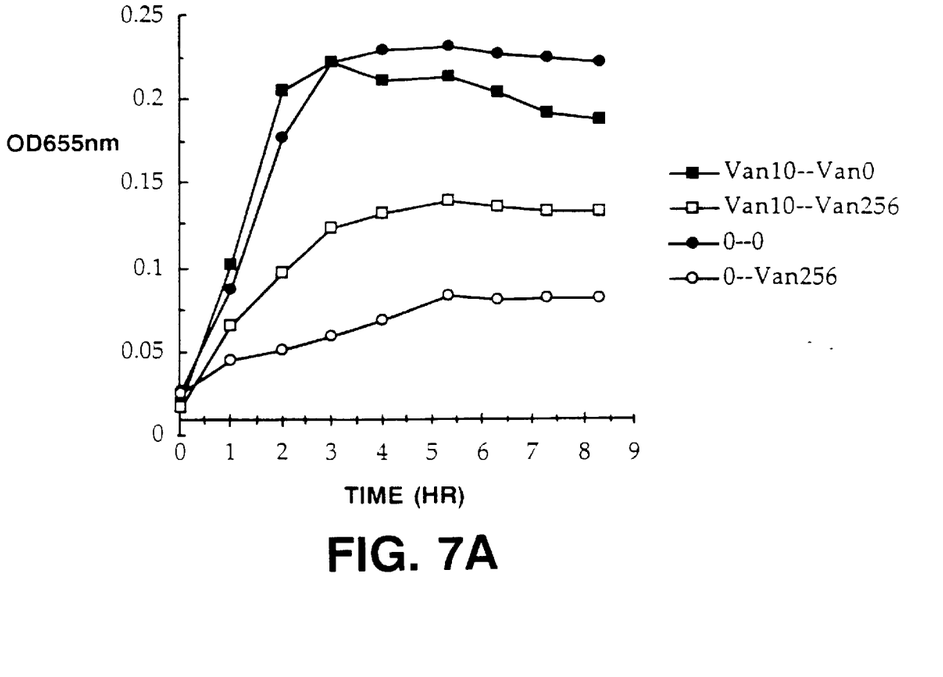
FIG. 7B is a line graph depicting the induction of A256 cells by AA15352. Filled squares (AA15352–Van0) plot the optical density, over time, of an A256 culture that was grown overnight in BHI medium containing 1.25 µg/ml AA15352 and shifted to vancomycin-free BHI medium. Open squares (AA15352–Van256) plot the optical density, over time, of an A256 culture that was grown overnight in BHI medium containing 1.25 µg/ml AA15352 and shifted to BHI containing 256 µg/ml of vancomycin. Closed circles (0–0) and open circles (0–Van256) represent the same conditions as described in FIG. 7A.
Figure 7B:
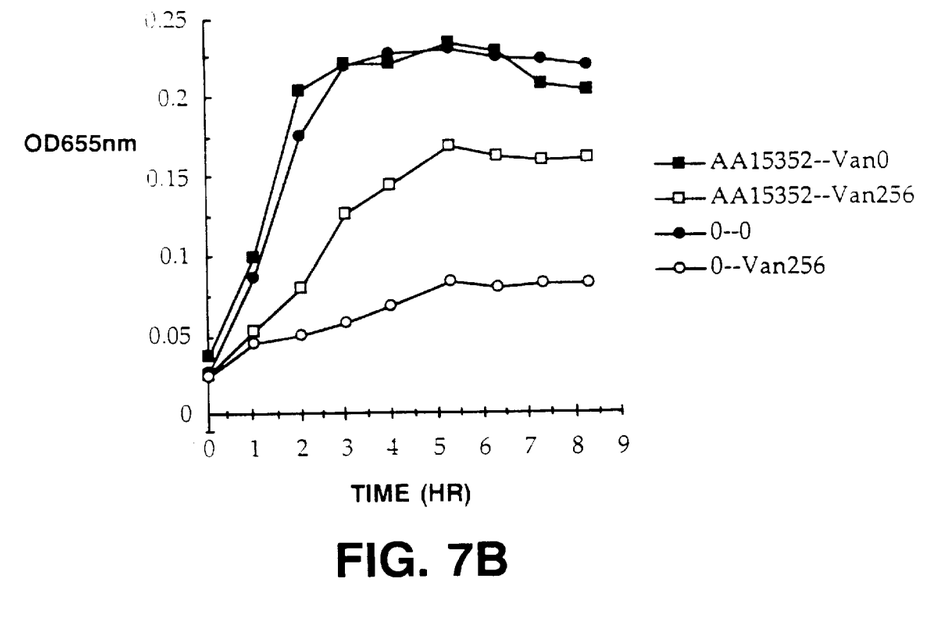

FIGS. 7A and 7B show that both vancomycin and extracts from cultures of AA15352 reduced the lag phase of growth. Therefore, the extract contains a compound capable of inducing vancomycin resistance.

The assay described above, where strains were tested for vancomycin-resistance by adding sub-inhibitory concentrations of vancomycin or moenomycin, was modified by transfecting the cells with a construct bearing a reporter gene (e.g., β-galactosidase, luciferase, alkaline phosphatase, or any other reporter gene known to skilled artisans) under the control of the van promoter. This modification allows production of a bacterial strain that will express the reporter gene product in response to compounds that inhibit bacterial cell wall synthesis. This assay is advantageous in that it allows detection of an inhibitor even if its concentration is above the MIC for the organism. Thus, inhibitors that would have been undetected previously, because they were present at concentrations high enough to inhibit bacterial grow, can now be detected by expression of the reporter gene. An assay dependent on reporter gene expression may also may be more sensitive in detecting cell wall inhibitors.

Isolation of the vanH Promoter and Preparation of a LacZ Fusion Construct

The vanH promoter was isolated by the polymerase chain reaction, using primers complementary to the known sequence of the van genes, and ligated into the vector pSKΔ6, obtained from Dr. Ruth Schmidt at Myco Pharmaceuticals, so that the vanH promoter was placed upstream from the lacZ gene. This fusion construct was digested and ligated into the plasmid pDL278, which contains an origin that replicates in Enterococcus, and the spectinomycin resistance gene, which can be exploited to select transformants.

Assay of Transfected MDD212 Cells

The MDD212 cell line is a derivative of *E. faecalis* strain OG1RF that carries the plasmid pDL278, described above, and the vancomycin resistance determinants vanR and vanS, which are essential for induction. MDD212 cells were transformed by electroporation, and successfully transformed cells were selected in the presence of 1 mg/ml spectinomycin. Other methods of transformation known to skilled artisans may also be employed. The vancomycin resistance determinant from A256, carrying the vanR and vanS regulatory genes, was mated into the transformed strain and the donor strain was counterselected by including rifamapicin and fusidic acid. The resulting strain was induced when cells were exposed to vancomycin, moenomycin, or thielavin B, which were all active. In addition, the activities of moenomycin and thielavin B were found at considerably broader ranges of concentration because enzyme activity, rather than viability, was measured.

Frozen stocks of transformed MDD212 cells (cryoprotected with 30% glycerol) were prepared according to standard methods. This stock was used to inoculate a liquid culture of BHI medium with spectinomycin that was incubated for 2–3 hours, with shaking, at 37° C. The cultured cells were aliquoted into a microtiter plate, the OD at 650 nm was measured, the background OD was subtracted, and the cultures were diluted to an OD of 0.01. Samples of fungal extract were added and the cultures were incubated at 37° C. for 2–3 hours. Following incubation, 20 $\mu$l of cells were added to 80 $\mu$l of Z buffer, and a series of two-fold dilutions were made. Ten $\mu$l of ONPG (4 mg/ml) was added to each well and incubation was continued at 30° C. Cultures containing vancomycin were incubated for 5 minutes, and cultures containing other samples were incubated for 1 hour. To terminate the enzymatic reaction, 30 $\mu$l of 1M $Na_2CO_3$ was added to each reaction. The OD at 405 nm was read with a Molecular Devices Thermo Max plate reader.

Analysis of β-glactosidase Activity

The OD at 405 nm of a culture containing Z buffer alone is approximately 0.06. Thus, this value was subtracted from the OD reading in each well to obtain an adjusted value. The adjusted values obtained for test samples were compared to the adjusted values obtained for untreated cells and cells treated with control compounds.

Figure 8A:
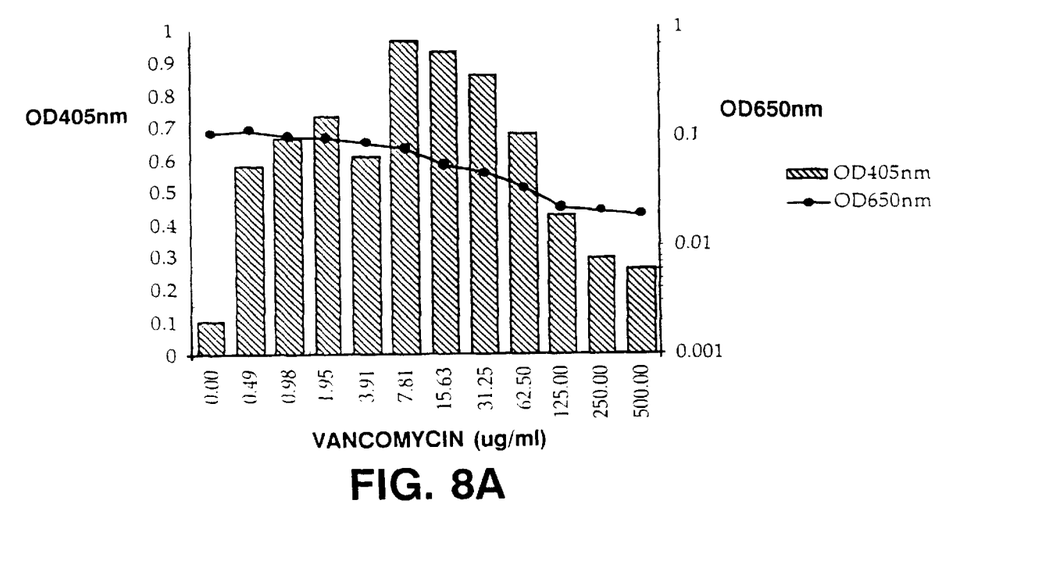
FIG. 8A is a bar graph showing the optical density of a culture of MDD212 cells at 405 nm, which reflects β-galactosidase activity, and at 650 nm, which reflects the growth of the culture, following exposure to varying concentrations of vancomycin.
Figure 8B:
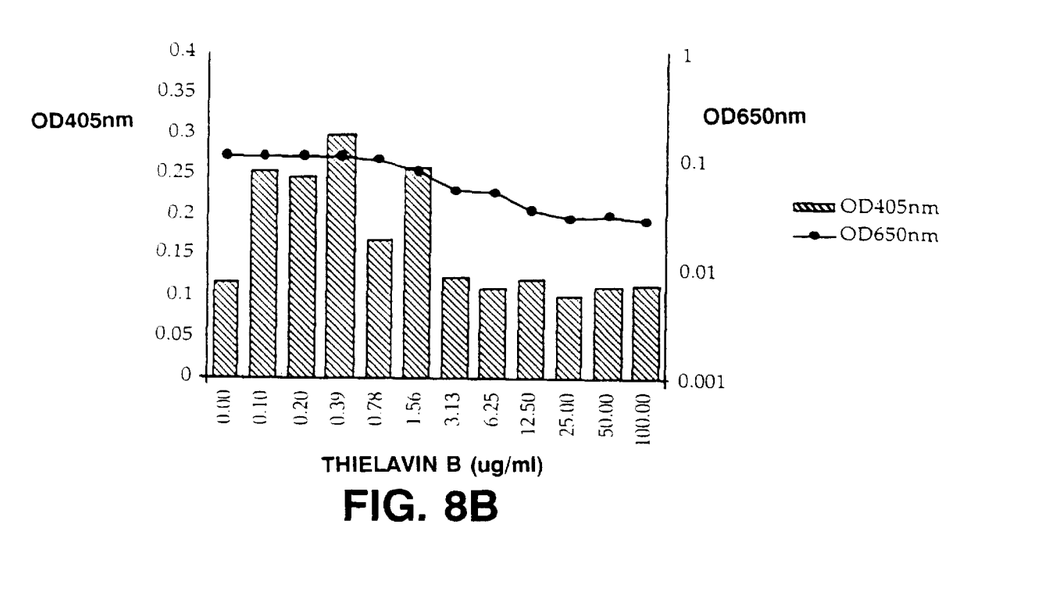
FIG. 8B is a bar graph showing the optical density of a culture of MDD212 cells at 405 nm, which reflects β-galactosidase activity, and at 650 nm, which reflects the growth of the culture, following exposure to varying concentrations of AA15352.

Vancomycin (shown in FIG. 8A), AA15352 (shown in FIG. 8B), and moenomycin (data not shown) induced β-galactosidase activity in MDD212 cells. Several other antibiotics, which are not known to be inhibitors of transglycosylation, were also tested. These included ampicillin, tetracycline, chloramphenicol, kanamycin, erythromycin, fosfomycin, fusidic acid, gentamicin, and D-cycloserine. None of these antibiotics caused induction of β-galactosidase.

The use of a reporter gene regulated by the van promoter provides a novel assay for compounds that inhibit bacterial cell wall synthesis. These experiments demonstrated that moenomycin, which is not structurally related to vancomycin, also induces the van genes. Therefore, it is likely that other compounds capable of inhibiting cell wall biosynthesis will also be detected.

Use

It is an object of the invention to provide therapeutically effective concentrations of the compounds 15352A, 15352B, thielavin A, thielavin B, and thielavin C for use in treatment of bacterial infections in animals, including humans. Such treatment includes administering a pharmaceutically effective amount of a composition containing one or more of the compounds disclosed herein to a subject in need of such treatment, thereby inhibiting bacterial growth. The composition may contain from about 0.1 to 90% by weight (such as about 1 to about 20% or about 1 to about 10%) of an active compound of the invention.

Solid formulations of the compositions for oral administration may contain suitable carriers or diluents such as corn starch, gelatin, lactose, acacia, sucrose, microcrystalline cellulose, kaolin, mannitol, dicalcium phosphate, calcium carbonate, sodium chloride, and alginic acid. Liquid formulations of the compositions for oral administration may be prepared in water or other aqueous vehicles and may contain various suspending agents that are well known to skilled pharmacologists. Injectable formulations of the compositions are also within the scope of the current invention and such formulations may contain various physiologically acceptable diluents or carriers known to skilled artisans.

The percentage of the active ingredient in each pharmaceutical formulation varies according to the formulation itself and the therapeutic effect desired in the specific pathologies and correlated therapeutic regimens.

The effective amount of the active compound used to practice the present invention for treatment of conditions caused by or contributed to by bacterial infection varies depending upon the manner of administration, the age, weight, and general health of the subject treated, and ultimately will be decided by the attending physician or veterinarian.

What is claimed is:

1. A compound having the stucture of compound 15352A.
2. An antibiotic preparation consisting essentially of the compound of claim 1.
3. A compound having the stucture of compound 15352B.
4. An antibiotic preparation consisting essentially of the compound of claim 3.
5. A method of treating a bacterial infection in a mammal, said method comprising administering to said mammal a therapeutically effective amount of the compound of claim 1 or claim 3.
6. A method of treating a bacterial infection in a mammal, said method comprising administering to said mammal a therapeutically effective amount of thielavin A, thielavin B, or thielavin C.
7. A method for detecting antibacterial activity, said method comprising:
   (a) culturing vancomycin-dependent bacterial cells that have been transfected with a construct bearing a reporter gene under the control of a van promoter,
   (b) exposing said culture to the broth of a fungal culture, a homogenate of the fungal culture, or a fungus,
   (c) incubating said exposed cells, and
   (d) performing a procedure to detect the expression of said reporter gene, said expression indicating the presence of an antibacterial compound.

* * * * *